United States Patent [19]
Audeh et al.

[11] Patent Number: 5,141,724
[45] Date of Patent: Aug. 25, 1992

[54] MERCURY REMOVAL FROM GASEOUS HYDROCARBONS

[75] Inventors: Costandi A. Audeh, Princeton, N.J.; Barry E. Hoffman, Kirkland, Canada

[73] Assignee: Mobil Oil Corporation, Fairfax, Va.

[21] Appl. No.: 772,179

[22] Filed: Oct. 7, 1991

[51] Int. Cl.$^5$ ............................................. B01D 47/00
[52] U.S. Cl. ...................................... 423/210; 55/72; 55/35
[58] Field of Search ....................... 55/35, 72; 423/210

[56] References Cited

U.S. PATENT DOCUMENTS

| | | | |
|---|---|---|---|
| 3,626,666 | 12/1971 | Drinkard | 55/67 |
| 4,892,567 | 1/1990 | Yan | 55/72 |
| 4,982,050 | 1/1991 | Gammie et al. | 585/818 |

OTHER PUBLICATIONS

Kirk–Othmer 15 Encyclopedia of Chemical Technology 623–629 (3rd Edition).

*Primary Examiner*—Bernard Nozick
*Attorney, Agent, or Firm*—Alexander J. McKillop; Charles J. Speciale; Jessica M. Sinnott

[57] ABSTRACT

Mercury is removed from a gaseous hydrocarbon stream by passing the stream through an in-line mixer which includes mixing elements which have gas-contacting surfaces of an amalgam-forming metal. Preferred amalgam-forming metals are gold, silver or a combination thereof. A specific in-line mixer has static mixing elements which are disposed along the length of the mixer, preferably, the mixing elements are helically disposed along the length of the mixer. Other contaminants such as water and residual $H_2S$ and $CO_2$ are removed from the gas stream by a gas purification system which includes the in-line mixer and a desiccant bed modified for removing mercury and other contaminants. The modifications to the desiccant bed include a porous gold and/or silver containing layer, i.e., a gold and/or silver wire screen or packed gold and/or silver wool, and a protective layer of alumina pellets having an active compound such as copper hydroxide, copper oxide and copper sulfide impregnated therein.

10 Claims, 1 Drawing Sheet

MERCURY REMOVAL FROM GASEOUS HYDROCARBONS

FIELD OF THE INVENTION

The invention is directed to a method of removing residual mercury from hydrocarbon gases. More specifically, the invention is directed to a special in-line mixer which has gold and/or silver on the gas-contacting portions and a process which employs the in-line mixer to remove residual mercury from hydrocarbon gases. Even more specifically, the invention relates to a method of using the in-line mixer and a modified desiccant bed to remove residual mercury from hydrocarbon gases.

BACKGROUND OF THE INVENTION

Natural gas which is produced from a natural gas well is usually separated and purified to provide products for a variety of end uses. The high-pressure mixture produced from the well, i.e. the wellstream, is typically sent to a separator vessel or a series of separator vessels maintained at progressively lower pressures where the wellstream is separated into a gaseous fraction and a liquid fraction.

The gaseous fraction leaving the separator, which may contain impurities such as mercury, carbon dioxide and hydrogen sulfide, is sent to a gas treatment and purification plant where the mercury concentration is normally reduced to $<0.1$ micrograms/Nm$^3$, the $CO_2$ concentration is reduced to the parts per million (ppm) level, and the $H_2S$ to about one (1) ppm.

The purification of the gaseous fraction is commonly achieved by passing the gaseous fraction over a bed of activated carbon which has been impregnated with sulfur. In this step, the mercury in the gas reacts with the sulfur and is essentially removed from the gaseous fraction. The mercury content of the gas can be reduced from about 250 micrograms/Nm$^3$ or higher to less than about 0.1 micrograms/Nm$^3$.

The gas leaving the sulfur/carbon bed then could be treated with a hot aqueous potassium carbonate solution which has the ability to absorb $CO_2$ and $H_2S$. This step produces a natural gas stream having a reduced $CO_2$ and $H_2S$ content. For example, the $CO_2$ content of the gas can be reduced from about 15% to about 0.3% and the $H_2S$ content from about 80 ppm to about 6 ppm.

The natural gas stream which resulted from treatment with the carbonate solution is further treated in order to reduce the amount of $CO_2$ and $H_2S$ by treating the gas with an amine solution, e.g. an aqueous solution of diethanolamine. Diethanolamine has the ability to absorb $CO_2$ and $H_2S$, and can reduce the $CO_2$ content from about 0.3% to about 50 ppm, and the $H_2S$ content from about 6 ppm to about 1 ppm. The natural gas is then washed with water to remove traces of entrained amine. This water wash, however, neither removes residual mercury (typically present in levels of less than 0.1 $\mu g$/Nm$^3$) nor residual $H_2S$ and $CO_2$ (typically about 1 ppmv and 50 ppmv) respectively.

The washed natural gas is water-saturated and has to be dried prior to liquefaction. Usually drying is achieved by contacting the wet gas with a desiccant in a parked bed specifically designed for this purpose. The desiccant bed undergoes repeated cycles of adsorption and regeneration. To ensure that the desiccant bed retains its integrity during the drying and regeneration cycles, a protective layer of inert alumina spheres having a depth of about 0.5–2 ft. is placed over the desiccant. The alumina spheres in the protective layer are somewhat larger than the desiccant particles.

The dried gas, which still contains small amounts of mercury, $CO_2$ and $H_2S$, can be further purified by contacting it with an adsorbent bed comprising sulfur on carbon, which has the ability to selectively remove mercury from the gas. Usually such an adsorbent can reduce the mercury, concentration to less than about 0.01 $\mu g$/Nm$^3$. However, including such an additional bed causes a pressure drop in the system, which is undesirable in a system where elevated pressure is required for maximum efficiency.

Thus, it would be beneficial to provide a mechanism for further reducing the level of residual mercury from the gas leaving the desiccant bed without the additional pressure reduction resulting from the use of a second adsorbent bed. It would also be very desirable to remove residual $CO_2$ and $H_2S$ from the gas.

It is therefore an object of the present invention to provide an improved method for reducing residual levels of mercury from a gas stream.

SUMMARY OF THE INVENTION

The instant invention facilitates removal of residual mercury from a gaseous hydrocarbon fraction by bringing the gas into contact with an in-line mixer which has gas contacting surfaces that remove the mercury from the gas. The gas-contacting mixing elements are of an amalgam-forming metal. The amalgam-forming metal removes the mercury from the gas as it passes through the mixer. The process removes the mercury without imposing high pressure loss on the stream and eliminates the need for a separate downstream adsorbent bed for removing residual mercury.

The invention is directed to a process for the removal of mercury and moisture from a gaseous hydrocarbon fraction comprising the steps of drying the gaseous hydrocarbon fraction in a desiccant bed which includes at least one impregnated substrate selected from the group consisting of a first substrate impregnated with copper oxide, a second porous substrate impregnated with copper hydroxide and a third porous substrate impregnated with copper sulfide and the desiccant bed additionally includes a pourous layer containing a member selected from the group consisting of silver, gold or a mixture thereof; conveying said dried gaseous hydrocarbon fraction to a mercury removal zone which includes an in-line mixer comprising a plurality of gas-contacting mixing elements having gas-contacting surfaces of silver or gold or a combination thereof, the mixing elements are positioned to contact the gaseous hydrocarbon fraction; and discharging the gaseous hydrocarbon fraction from the mercury removal zone whereby the gaseous hydrocarbon fraction is substantially free of mercury.

The process also includes the steps of purifying the gaseous fraction with a solution which absorbs carbon dioxide and hydrogen sulfide, such as carbonate and diethanolamine, and washing to remove entrained absorbent solution and provide a substantially absorbent solution-free stream.

DETAILED DESCRIPTION

The invention is directed to an apparatus for removal of residual mercury from a gas stream by bringing the gas stream into contact with an in-line mixer which contains static mixing elements having gas contacting surfaces of an amalgam-forming metal. The invention is also directed to a process of removing mercury from a gaseous hydrocarbon fraction in which the gaseous hydrocarbon fraction is conveyed to a gas purification zone which includes an in-line mixer containing a plurality of static gas-contacting mixing elements having gas-contacting surfaces of an amalgam-forming metal. Preferably, the amalgam-forming metal is silver, gold or a combination thereof.

Figure 1:
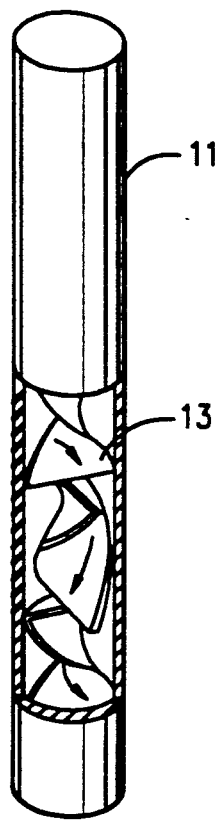
FIG. 1 illustrates an apparatus suitable for practice of the invention.
Figure 2:
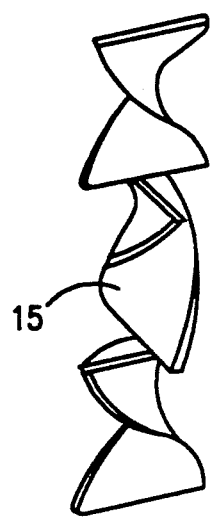
FIG. 2 illustrates the static mixing elements which are characteristic of one embodiment of the invention.

In one embodiment, shown in FIG. 1, an apparatus for removing residual mercury is a cylindrical column 11. The cylindrical column is fitted with a plurality of static mixing elements or baffles 13 disposed along the length of the cylinder. The static mixing elements are helically arranged and extend across the diameter of the column. The configuration of the helically arranged static mixing elements 15 is more clearly shown in FIG. 2 where it will be seen that the the stream flowing through the column will be deflected by a first static mixing element and will divide when the stream reaches each successive mixing element.

The in-line mixer contemplated can be of any type known in the art in which gas-contacting surfaces of the static mixing elements can be gold, silver or a combination thereof. Such in-line mixers contain static mixing elements that are in the form of loosely crumpled ribbons or organized spirally arranged ribbons. Specific examples of such mixers are described in Kirk-Othmer's *Encyclopedia of Chemical Technology*, Vol. 15, p.p. 623–624 which is incorporated herein by reference.

The gas-contacting surfaces of the mixing elements are, preferably, made of silver, gold or a combination thereof. Passing a gas stream containing mercury over these mixing elements efficiently removes the mercury. The mercury present in the stream interacts with the gold or silver and forms an amalgam with the amalgam-forming metal as the gas passes through the mixer. After the mixing elements are fully amalgamated; that is, when the ability of the gold and/or silver to remove mercury from the gas is exhausted, the mixing elements can be regenerated by exposure to heat at temperatures ranging from 400° to 800° C., preferably 500° to 700° C.

Figure 3:
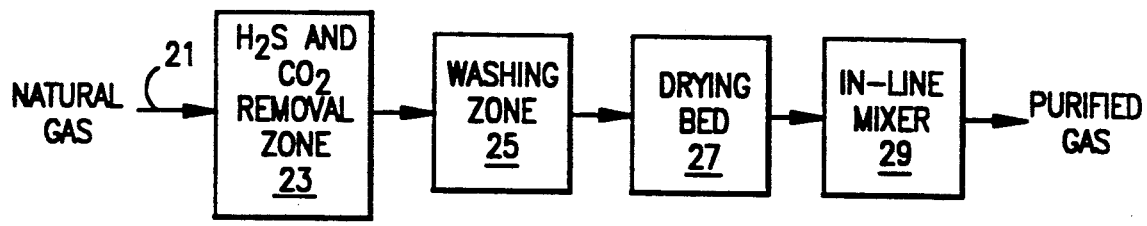
FIG. 3 is a simplified schematic flow diagram of one embodiment of the gas purification process of the invention.

The in-line mixer can be part of a gas purification system in which the gaseous hydrocarbon fraction is conveyed to a gas purification zone which includes the in-line mixer. The gas purification zone can be specially designed to remove mercury and other contaminants from the gas stream and can include means for drying and for removing $H_2S$ and $CO_2$ as well. Referring to FIG. 3, the gas purification zone comprises an $H_2S$ and $CO_2$ removal zone 23, washing zone 25, drying bed 27 and in-line mixer 29. A natural gas is conveyed via line 21 to the $H_2S$ and $CO_2$ removal zone 23. The $H_2S$ and $CO_2$ removal zone employs a solution which absorbs these components, such as a hot aqueous potassium carbonate followed by treatment with an amine, such as an aqueous solution of diethanolamine to further absorb $CO_2$ and $H_2S$. Thereafter, the gas is washed in washing zone 25. In the washing zone the gas is washed with water to remove traces of entrained amine. The water saturated gas is then passed to a drying bed 27. The drying bed is designed to dry the gas. In accordance with a preferred embodiment of the invention, as indicated above, the drying bed can include a desiccant bed which includes at least one impregnated substrate selected from the group consisting of a first substrate impregnated with copper oxide, a second porous substrate impregnated with copper hydroxide and a third porous substrate impregnated with copper sulfide, the desiccant bed additionally includes a porous layer containing a member selected from the group consisting of silver, gold or a mixture thereof. This bed is designed to remove residual mercury. Therefore, the invention also provides for an optional dehydration desiccant bed which includes, as part of the drying bed 27, layers for removal of residual mercury, $H_2S$ and $CO_2$. The dried gas is then conveyed from drying bed 27 to the in-line mixer 29 which is designed to remove the last amount of mercury remaining in the gas.

In a preferred embodiment of the invention the in line mixer is part of a gas purification process which includes a desiccant bed having at least one porous silver and/or gold-containing layer coupled with a protective layer. The protective layer comprises inert materials, such as alumina pellets. At least a portion of the inert materials are impregnated with at least one active compound. Examples of suitable active compounds include the following compounds: copper hydroxide, copper oxide or copper sulfide. The active compound provides the desiccant bed with the additional capability of removing residual $H_2S$ and $CO_2$, as well as mercury, from the gaseous fraction without incurring the pressure loss inherent in utilizing a separate downstream adsorbent bed for removal of the mercury.

Preferably, the in-line mixer of the invention is located downstream of the desiccant bed. The in-line mixer can be considered a guard bed against residual mercury passing to the downstream equipment. The gas, which is dry and has had most of the contaminants removed, contacts the mixing elements of this apparatus; thus, the apparatus effectively removes the last amount of mercury remaining in the gas.

The porous silver and/or gold-containing layer of the desiccant bed may be in the form of a screen, woven from wire having silver and/or gold on the gas contacting surfaces. The screen is woven to from about 4 to about 80 size mesh, preferably from about 10 to 30 size mesh and most preferably into a screen having about a 20 size mesh. Alternatively, the porous silver and/or gold-containing layer may be in the form of loosely packed silver and/or gold wire or silver and/or gold "wool". A key to the method of the present invention and apparatus, therefore, is that the gas stream can pass through the silver and/or gold containing layer of the desiccant bed and the in-line mixer without incurring a large pressure drop which is inherent when utilizing separate and additional downstream packed mercury removal beds.

The porous silver and/or gold containing layer may be composed of more than one type of the above-described porous elements. For example, the porous silver and/or gold-containing layer may include a silver-containing screen, a gold-containing layer may include a silver-containing screen, a gold-containing screen and/or loosely packed silver wire or "wool", and/or other forms of porous silver and/or gold-containing materials. The porous silver and/or gold layer may be disposed above and/or below the desiccant in the desiccant bed. In a preferred embodiment, however, the desiccant bed includes both a porous silver and/or gold layer disposed above the desiccant as well as another porous silver and/or gold layer disposed below the desiccant.

According to one embodiment of the present invention, the protective layer of inert alumina pellets or spheres, which are usually placed on top of a desiccant bed to ensure that the desiccant bed retains its integrity during drying and regeneration, are replaced with similar size alumina pellets or spheres which have been separately impregnated with at least one of the following compounds: copper hydroxide, copper oxide, or copper sulfide. A separate porous silver and/or gold-containing layer may then be placed above the alumina pellets or spheres.

While alumina in the form of pellets is a preferred porous substrate of the present invention, other substrates may also be utilized including silica, silica-alumina, molecular sieves, silica gels, known porous substrates, and combinations thereof.

The desiccant of the present invention may comprise any solid which has the ability to adsorb water and release it upon heating to regenerate the desiccant. Such solids include silica gels and molecular sieves and combinations thereof.

These active compounds, namely the copper hydroxide, copper oxide, and copper sulfide, are most preferably impregnated into separate pellets. Thus, some of the pellets will be impregnated with copper hydroxide while others will be impregnated with copper oxide, and still others will be impregnated with copper sulfide. While it is preferred that the entire protective layer of alumina pellets is impregnated with one or more of these reactive substances, some of the pellets may remain untreated and are, thus, inert pellets in the protective layer.

Any known method for impregnating the porous substrate with these active compounds may be utilized. For example, the copper hydroxide impregnated alumina pellets may be prepared by thoroughly mixing 30 parts by weight of alumina (dry basis) with 8 parts copper hydroxide and 62 parts of deionized water extruding the mixture through a ¼ inch dieplate and drying at 120° C. The copper oxide impregnated pellets may be prepared by heating the copper hydroxide impregnated pellets to 400° C. The copper sulfide impregnated pellets may be prepared by reacting the copper hydroxide impregnated pellets with gaseous hydrogen sulfide. The present invention is not limited by the manner in which the active compounds are impregnated onto a substrate, nor the size nor shape of the material being impregnated.

When copper oxide is added to a substrate, it is preferably added in an amount of about 10-20% by weight of said substrate, most preferably about 12-18%. Similarly, copper hydroxide is preferably added in an amount of about 10-30% by weight based on the weight of the substrate, and most preferably in an amount of about 15-20% by weight. Lastly, when copper sulfide is utilized, it is preferably added in an amount of 10-20% by weight of the substrate, most preferably in an amount of about 12-18% by weight.

While the active compounds of the present invention are preferably impregnated into a porous substrate, these compounds may be dispersed on a non-porous substrate or may even be formed into hardened pellets themselves and placed on top of the desiccant bed. Although those skilled in the art will also appreciate that certain porous substrates will provide the added advantage of having the ability to absorb some moisture from the moisture-containing gas thereby supplementing the dehydration performed by the desiccant.

According to one preferred embodiment of the present invention, the ratio of each type of pellet, in other words the ratio of pellets impregnated with copper hydroxide to the number impregnated with copper oxide to the number impregnated with copper sulfide, is about 1:1:1. However, other ratios are possible without departing from the scope and intent of the present invention.

Copper sulfide has the ability to remove mercury from natural gas while allowing the adsorbed mercury to be stripped off during the desiccant regeneration cycle (heating with a gas sweep to about 500°-700° F.). Hence, the copper sulfide is periodically and simultaneously regenerated with the desiccant. Thus, in addition to supplying integrity to the desiccant bed, the CuS-impregnated alumina spheres remove mercury from the gas. The copper hydroxide and copper oxide not only have the ability to react with residual $CO_2$ and $H_2S$ to remove them from the gas, but by forming copper sulfide, also assist in reducing the level of mercury in the gas.

The present invention advantageously does not require substantial changes to new or existing gas treatment processes. The benefits of the present invention may be obtained while supplying the contaminated, moisture-containing natural gas to the modified desiccant bed at a pressure of about 1-100 atmospheres, at a temperature of about 50°-120° F. and at a space velocity of about 1-300 and then to the in-line mixer. Most preferably, the contaminated, moisture-containing gas is fed into the desiccant bed at a pressure of about 20-60 atmospheres, a temperature of about 60°-110° F., and at a space velocity of about 100-200 before passing to the in-line mixer. Those skilled in the art will appreciate that the space velocity is defined as the volume of gas passing through the desiccant bed every hour divided by the volume of the desiccant bed. As used herein, the volume of the desiccant bed is considered to be the sum of the volume of the desiccant and the total volume of pellets whether treated with one of the above mentioned compounds or untreated and left in an inert state.

As mentioned above, the desiccant bed can be regenerated by passing a gas such as methane, ethane or propane, through the desiccant bed at a temperature of about 400°-700° F., most preferably at a temperature of about 600° F. This regeneration step advantageously decomposes accumulated copper carbonate into carbon dioxide and copper oxide. The carbon dioxide is also advantageously carried away with the regenerating gas while the copper oxide remains in the alumina pellets for future use in removing contaminants from the natural gas.

Although the present invention is preferably used in a natural gas purification plant, the gas purification system of the present invention may also be utilized in the treatment of other gases such as hydrogen, ethylene, etc.

What is claimed is:

1. A process for the removal of mercury and moisture from a gaseous hydrocarbon fraction comprising the steps of drying the gaseous hydrocarbon fraction in a desiccant bed which includes at least one impregnated substrate selected from the group consisting of a first substrate selected from the group consisting of a first substrate impregnated with copper oxide, a second porous substrate impregnated with copper hydroxide and a third porous substrate impregnated with copper sulfide and the desiccant bed additionally includes a porous layer containing a member selected from the group consisting of silver, gold or a mixture thereof;

conveying said dried gaseous hydrocarbon fraction to a mercury removal zone which includes an in-line mixer comprising a plurality of gas-contacting mixing elements having gas-contacting surfaces of silver or gold or a combination thereof, the mixing elements are positioned to contact the gaseous hydrocarbon fraction; and discharging the gaseous hydrocarbon fraction from the mercury removal zone whereby the gaseous hydrocarbon fraction is substantially free of mercury.

2. The process for removing mercury as described in claim 1 including the steps of:

purifying the gaseous fraction with a solution which absorbs carbon dioxide and hydrogen sulfide; and washing the purified gas to remove entrained absorbent solution and provide a substantially absorbent solution-free stream.

3. The process as described in claim 2 in which the gas is washed with water.

4. The process as described in claim 2 in which the purifying solution is a carbonate.

5. The process as described in claim 4 in which the carbonate is aqueous potassium carbonate.

6. The process as described in claim 4 in which the purifying solution further includes an amine.

7. The process as described in claim 6 in which the amine is diethanolamine.

8. The process as described in claim 1 in which the mixing elements are static mixing elements.

9. The process of claim 8 in which the static mixing elements are baffles disposed along the length of the mixer.

10. The process as described in claim 9 in which the static mixing elements are baffles helically disposed along the length of the mixer.

* * * * *